United States Patent [19]

Plummer et al.

[11] 4,416,021
[45] Nov. 15, 1983

[54] X-RAY EXAMINATION APPARATUS

[75] Inventors: Steven J. Plummer, Middlefield; James E. Wieloch, Southington, both of Conn.

[73] Assignee: Siemens Corporation, Iselin, N.J.

[21] Appl. No.: 349,761

[22] Filed: Feb. 18, 1982

[51] Int. Cl.³ .............................................. G03B 41/16
[52] U.S. Cl. .................................... 378/181; 378/197
[58] Field of Search ............... 378/196, 197, 181, 177, 378/178, 179, 180

[56] References Cited

U.S. PATENT DOCUMENTS 2,488,315 11/1949 Morgan ............................... 378/197
2,997,585 8/1961 Schering ............................. 378/196

FOREIGN PATENT DOCUMENTS 2141461 2/1973 Fed. Rep. of Germany .

OTHER PUBLICATIONS

"Ceiling Support 3D/3D-M For Attachment of X-Ray Tube Assemblies and Image Intensifiers," Published by Siemens Aktiengesellschaft, West Germany.

Primary Examiner—Craig E. Church
Attorney, Agent, or Firm—Karl F. Milde, Jr.

[57] ABSTRACT

The X-ray apparatus contains an X-ray tube and a transition device for moving the X-ray tube between a vertical and a horizontal emission position. A first film cassette tray may be provided for vertical exposures. A second film cassette tray is provided for horizontal exposures. The X-ray apparatus further contains a sprocket and chain mechanism for operationally connecting the second tray to the X-ray tube. This mechanism is designed such that the second tray is positioned in a waiting position outside the vertical X-ray beam when the X-ray tube is in its vertical emission position, and that the second tray is automatically transferred from the waiting position to a horizontal exposure position when the X-ray tube is moved from its vertical emission position to its horizontal emission position. The mechanism preferably contains a first sprocket connected to the rotation axis of the X-ray tube, a second sprocket connected to a common rotation axis, a third sprocket connected to the rotation axis of the second tray, a fourth sprocket also connected to the common rotation axis, and two chains, one of which chains reverses the rotation direction of the axis connected therewith.

8 Claims, 4 Drawing Figures

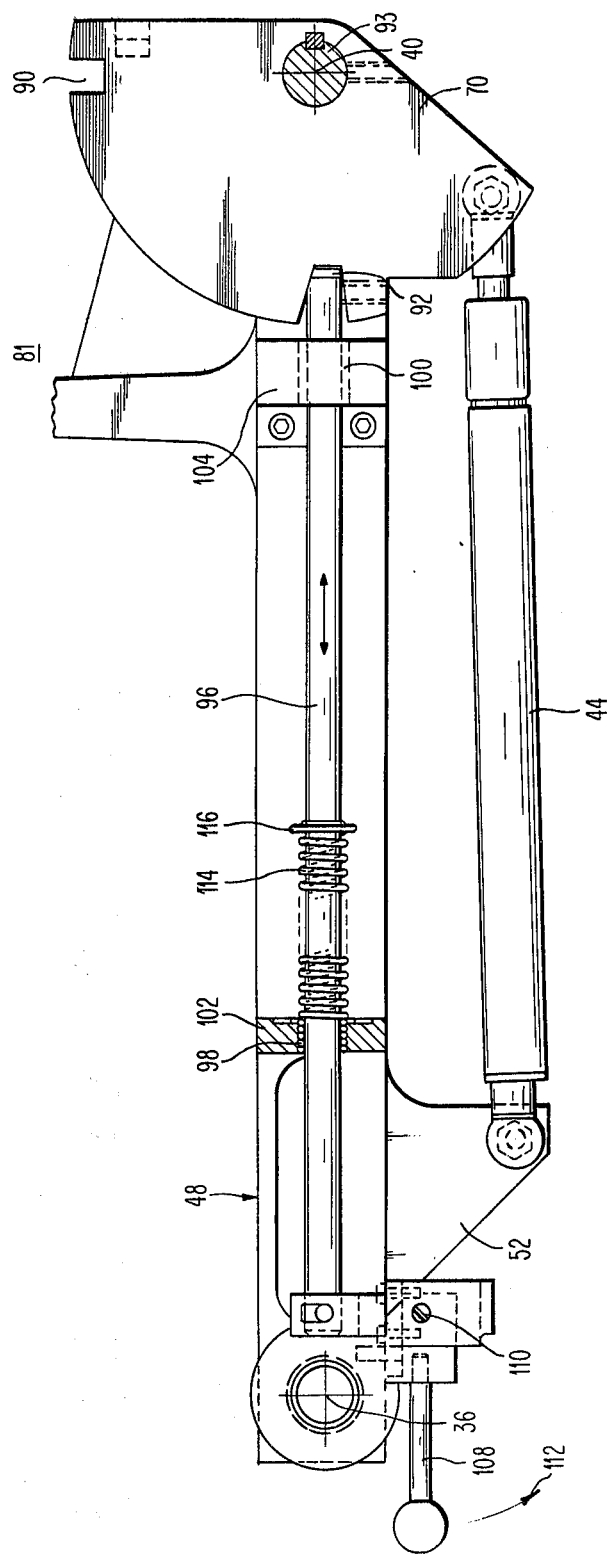

X-RAY EXAMINATION APPARATUS

CROSS REFERENCE TO RELATED APPLICATIONS

This invention relates to the same technical field as the commonly owned patent application entitled "X-Ray Examination Apparatus" by Winfried Platz and Steven Plummer, Ser. No. 312,621, filed on Oct. 19, 1981.

BACKGROUND OF THE INVENTION

1. Field of the Invention

This invention generally relates to X-ray apparatus having an X-ray tube and a film cassette tray for taking exposures in X-ray diagnosis. More particularly, this invention relates to an X-ray apparatus which is equipped for taking exposures in vertical and horizontal directions.

2. Description of the Prior Art

In the brochure "Ceiling Support 3D/3D-M for Attachment of X-ray Tube Assemblies and Image Intensifiers," published by Siemens Aktiengesellschaft, West Germany, is disclosed a ceiling support device which is designed as a carrier for an X-ray tube assembly and an image intensifier. This support device especially allows utilization of the X-ray tube assembly and the image intensifier in X-ray diagnosis. The ceiling support device is independent of any floor support. One of the main parts of the support device is a telescopic column or crane extending in a vertical direction from the ceiling. The telescopic column may be movable in longitudinal and transverse ceiling tracks. It may also be fixed to the ceiling so that only vertical movements are possible. For instance, the ceiling support device may be applied in connection with a bucky table. In one version of the known ceiling support (see FIG. 3 of the brochure "Ceiling Support 3D/3D-M," supra) a horizontally extending mounting arm is attached to the lower end of the column. The X-ray tube assembly which comprises an X-ray tube and a collimator is attached to one end of this mounting arm. Attached to the other end of the mounting arm is a control box. This box contains control switches, an angle indicator allowing oblique angles to be easily set and reproduced, a light beam indicator permitting exact alignment of a control beam with the center of a cassette tray located in the bucky table, and a tape measure showing the focus/film distance for radiographs using horizontal or oblique beam projections. Radiographs with vertical beam projection are also possible. The switches in the control box are lock releases for horizontal and vertical movements, a latch release for rotational movements, and a lock release for oblique settings.

The known ceiling support allows for X-ray exposures of a patient in a vertical and a horizontal direction. As already mentioned, a first film cassette tray is positioned in the table top beneath the patient. In another version the X-ray tube is located beneath the patient and the film cassette above the patient. This also allows for horizontal exposures, when the second film tray is used which is located in the bucky wall stand. It will be noted that the two trays are not operationally connected to each other.

In order to move the X-ray tube from a position where radiation is emitted in a vertical direction to a position where radiation is emitted in a horizontal direction, the X-ray tube assembly must be rotated about the longitudinal axis of the mounting arm. A cassette tray for horizontal exposures is provided in the separate lucky wall stand (see FIG. 4 of the brochure "Ceiling Support 3D/3D-M" supra). Such a tray is not provided on the column or on the mounting arm. In other words: the known ceiling support takes exposures in a vertical direction of radiation using the film cassette tray which is built into the bucky table. For horizontal exposures, the additional wall stand having built-in a second film cassette is required. Therefore, an apparatus equipped for horizontal and vertical exposures becomes expensive. In addition, switching from the vertical to horizontal radiation and exposure position is time consuming, since adjustment work is needed to position the second cassette in a vertical position in front of the X-ray tube assembly. Whenever this position is taken, the focus-film-distance has to be measured to determine the correct exposure time. Since the second film tray is arranged in a wallstand, access to the patient is limited especially when lateral exposures are to be taken.

In German Offenlegungsschrift or published application No. 21 41 461 is disclosed an X-ray apparatus containing a ceiling support device or column, an X-ray tube and a film cassette. To the lower end of the column is connected a transverse arm which pivots about an axis that is arranged perpendicularly to the longitudinal axis of the column. To one end of this transverse arm is pivotly connected a first support arm, to the free end of which is pivotally attached the X-ray tube. To the other end of the transverse arm is pivotally connected a second support arm to the free end of which is pivotally connected the film cassette. The pivoting axes of the first and second arms are parallel to the pivoting axis of the transverse arm. There is provided a driving mechanism by which, independently from the rotational position of the transverse arm, the orientation of the first support arm is maintained and by which the central beam of the X-ray beam is permanently kept parallel to the longitudinal axis of the arm. This X-ray apparatus is useful for many applications. However, due to its sophisticated driving mechanism, its production is too expensive for applications where X-ray exposures only in a horizontal and a vertical direction have to be taken. In addition, free access to the patient is limited, and problems may arise when a X-ray film tray is to be used instead of the X-ray image intensifier.

Frequently examinations are made of a patient's internal organs as for instance the stomach. In these examinations it is of interest to the physician to observe for example the action of a barium surry from the stomach wall of a patient resting on a stretcher or medical examination table. In these examinations, X-rays are taken laterally, that is transversely to the longitudinal axis of the resting patient. When the patient lies on his or her side, such exposure are taken in the direction from the front to the back, or vice versa, and when the patient lies on his or her back or stomach, such exposures are taken in the direction from the left side to the right side, or vice versa. This means that the cone of X-rays leaves the X-ray tube approximately horizontally and is received by an X-ray film which is positioned approximately vertically. It is desirable to have an X-ray apparatus which can be used for these examination, using horizontal irradiation, but which can easily be changed over such that conventional examinations using vertical irradiation can be performed.

SUMMARY OF THE INVENTION

1. Objects

It is an object of this invention to provide an X-ray apparatus, wherein an X-ray tube is used for vertical exposures as well as for horizontal exposures, wherein a first film cassette tray may be used for vertical exposures and a second film cassette tray is used for horizontal exposures, wherein a quick transition from a vertical exposure position to a horizontal exposure position, and vice versa, can easily be performed, and wherein access to a patient under X-ray examination is not impeded by the unused film cassette tray when exposures are to be taken.

It is still another object of this invention to provide an X-ray apparatus wherein the means for performing a transition from a vertical exposure position to a horizontal exposure position, and vice versa, are of simple design and do not include any protruding parts.

It is still another object of this invention to provide an X-ray apparatus wherein the means for performing transition from a vertical to a horizontal exposure position, and vice versa, are comparatively compact and can easily be covered by a casing.

2. Summary

According to this invention, an X-ray apparatus contains an X-ray tube and a transition device for moving the X-ray tube between a first and a second position. In the first position, the X-ray tube emits a beam of X-rays substantially in a vertical direction, and in the second position the X-ray tube emits a beam of X-rays substantially in a horizontal direction. A first film cassette tray may be provided for vertical exposures. The plane of this film cassette is positioned substantially horizontally such as to receive the vertical beam of X-rays from the X-ray tube when the X-ray tube is in its first position. This first cassette may be contained in an examination table. The X-ray apparatus contains a second film cassette tray. This second tray has a plane which in an exposure position is positioned substantially vertically such as to receive the horizontal beam of X-rays from the X-ray tube when the X-ray tube is in its second position.

The X-ray apparatus further contains a suitable position transfer device or mechanism such as a sprocket and chain mechanism for operationally connecting or attaching the second film cassette tray to the X-ray tube. By this sprocket and chain device the second film cassette tray is positioned in a waiting position outside the vertical beam of X-rays when the X-ray tube is in its first position. This sprocket and chain device is also designed for transferring the second film cassette tray from the waiting position to the exposure position when the X-ray tube is moved from its first position to its second position.

In other words: the second X-ray film cassette tray is automatically brought into the correct horizontal exposure position when the X-ray tube is moved from its first position into its second position. When the X-ray tube is in a vertical exposure position and is directed towards the first film cassette, the second film cassette tray is kept in a waiting position outside the beam of X-rays. Therefore, the second tray does not interfere with vertical exposures. In addition, it does not impede access to a patient subject to X-ray examination.

In particular, the X-ray tube, the second cassette tray and the transition device may be operationally connected to a support column which is mounted or suspended above the X-ray apparatus from a support beam or from the ceiling of the room.

Since the transition and the connection device contains an arrangement of chains and sprockets, it can be designed comparatively compact such that no parts protrude therefrom. Thus, it is easy to cover the device by any suitable kind of paneling.

The foregoing and other objects, features and advantages of the invention will be apparent from the following more particular description of the preferred embodiments of the invention, as illustrated in the accompanying drawings.

BRIEF DESCRIPTION OF THE DRAWINGS

In the drawings:

FIG. 4 is a side view of a locking device used in the X-ray apparatus illustrated in FIGS. 1 through 3.

DESCRIPTION OF THE PREFERRED EMBODIMENT

Figure 1:
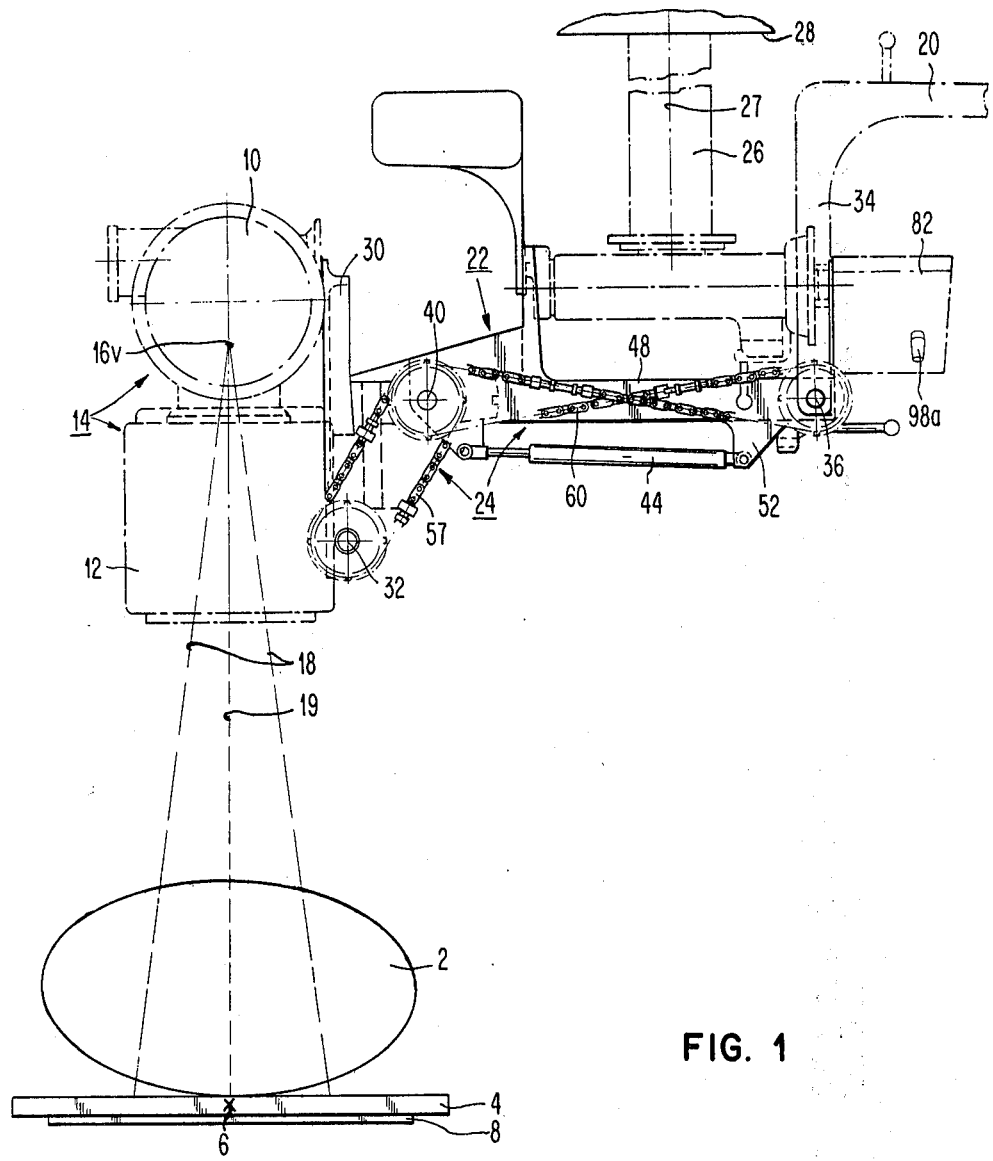
FIG. 1 is a schematic side view of an embodiment of an X-ray examination apparatus according to the invention, wherein the X-ray tube is in a vertical emission position, and wherein the second film cassette tray is in a non-use position.
Figure 2:
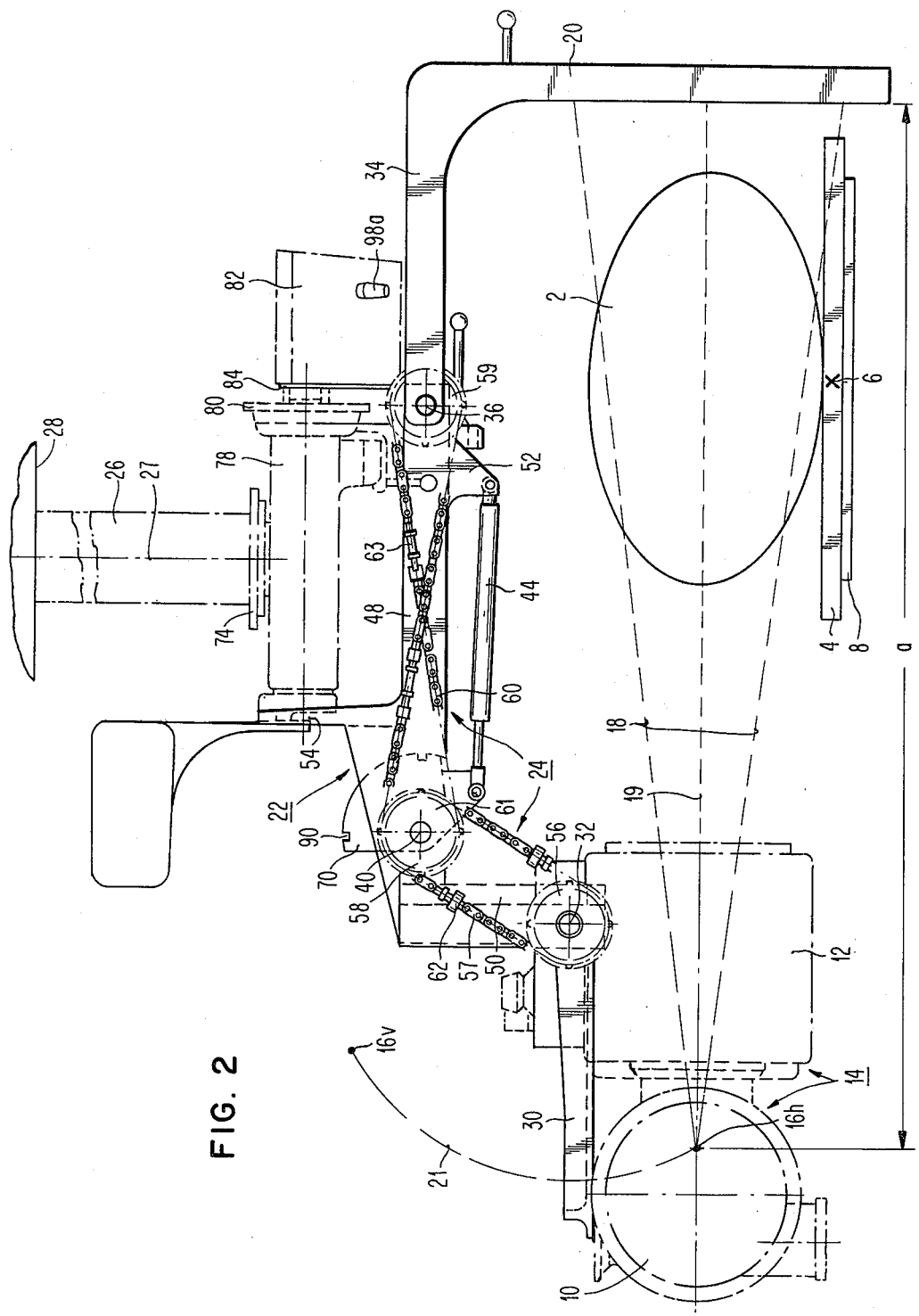
FIG. 2 is a schematic side view of the apparatus illustrated in FIG. 1, wherein the X-ray tube is in its horizontal emission position, and wherein the second film cassette tray is in its exposure position.

With reference to FIGS. 1 and 2 an X-ray apparatus is illustrated which can be used for taking vertical exposures as well as for horizontal exposures from a patient 2. The patient 2 lies on a table top 4 which is part of a conventional patient examination table. The table top 4 can be moved horizontally along its longitudinal axis 6 in a direction perpendicular to the plane of the drawing. The table top 4 or the whole table can also be moved in a horizontal direction perpendicular to the longitudinal axis 6.

To the lower side of the table top 4 is attached a first film cassette tray 8 for housing a film cassette therein.

One of the principal parts of the X-ray apparatus is an X-ray tube 10 which is combined with a collimator 12 to form a tube assembly 14. The focus of the X-ray tube 10 is denoted as 16. The X-ray tube 10 is used for vertical exposures as well as for horizontal exposures. Thus, according to FIG. 1, the X-ray tube 10 can assume a first position (see focus position 16v) in which it emits a diverging beam 18 of X-rays substantially in a vertical direction downwardly toward the patient 2 and the first film cassette tray 8. According to FIG. 2 the X-ray tube 10 can assume a second position (see focus position 16h) in which it emits a diverging beam 18 of X-rays substantially in a horizontal direction towards the patient 2. The central beam of the beam 18 is denoted by 19.

The first film cassette tray 8 is used for vertical exposures, as can be seen in FIG. 1. This first film cassette tray 8 has a plane which in its exposure position is positioned substantially horizontally such as to receive the vertical beam 18 of X-rays from the X-ray tube 10 when the X-ray tube 10 is in its first position.

There is also provided a second film cassette tray 20 which is used for horizontal exposures, as can be seen in FIG. 2. The second film cassette tray 20 has a plane which in its exposure position is positioned substantially vertically such as to receive the horizontal beam 18 of X-rays from the X-ray tube 10 when the X-ray tube 10 is in its second position.

In FIG. 1, the second film cassette tray 20 is positioned in a waiting or non-use position outside the vertical beam 18 of X-rays, and in FIG. 2 the second film cassette tray 20 is positioned in an exposure position, thereby receiving X-rays penetrating the body of the patient 2.

As will be described in more detail below, there is provided a first mechanism or transition device for moving the X-ray tube 10 from its first to its second position, and vice versa. There is also provided a second mechanism or transition device for transferring the second film cassette tray 20 from the waiting position to the exposure position, and vice versa, when the X-ray tube 10 is moved from its first position to its second position, and vice versa. In other words, a movement of the second film cassette tray 20 is coupled to a movement of the X-ray tube 10, and vice versa. Thus, the second film cassette tray 20 is automatically transfered from its waiting position into its horizontal exposure position when the X-ray tube 10 is moved from its vertical first position to its horizontal second emission position. Due to the fact that the waiting position of the second film tray 20 is chosen to be outside the path of X-rays and above the exposure position, the second film cassette tray 20 does not impede the access to the patient 2.

In FIG. 2, the position of the focus 16 during a vertical exposure is denoted by 16v, while its position during a horizontal exposure is denoted by 16h. Movement from one position to the other is along a quarter circle 21.

The transition devices for moving the X-ray tube 10 from its first to its second position and for simultaneously moving the second film cassette tray 20 from its waiting position into its exposure position, and vice versa, comprises a rigid arm assembly or mounting device 22 and a chain and sprocket assembly 24. The mounting device 22 is attached to the lower end of a support column 26. The support column 26 may be suspended from a support beam or a ceiling 28 in a vertical direction. Preferably the column 26 is a telescopic column of conventional design.

With respect to the longitudinal axis 27 of the support column 26, the mounting device 22 has a first or left side and a second or right side. The X-ray tube 10 is pivotally connected to the left side of the mounting device 22, while the second film cassette tray 20 is pivotally connected to the right side of the mounting device.

The X-ray tube 10 is attached to a first support arm or lever 30 and is tiltable about a first horizontal axis 32. The second film cassette tray 20 is connected to a second support arm or lever 34 and is tiltable about a second horizontal axis 36. The axes 32 and 36 are parallel to each other. The first axis 32 is vertically lower than the second axis 36. Both axes 32 and 36 are provided at the left and right end portion, respectively, of the mounting device 22. As can be seen from FIGS. 1 and 2, the X-ray tube 10 is rotated about the first horizontal axis 32 between its first and second position, and the second film cassette tray 20 is rotated about the second horizontal axis 36 between its waiting position and its exposure position.

Coordination of both movements is performed by means of the chain and sprocket assembly 24. The chains of this assembly 24 are rotatable about a third horizontal pivoting axis or common pivotal axis 40. The third horizontal pivoting axis 40 is parallel to the axes 32 and 36 and may be located on the same horizontal plane as the second axis 36.

Operation of the chain and sprocket assembly 24 which operatively connects the second film cassette tray 20 to the X-ray tube 10 may be by hand. That is, the operator (physician, technician) rotates the second film cassette tray 20 about the second horizontal axis 36, and a rotation of the X-ray tube 10 about the first horizontal axis 32 will automatically follow. This operation can be facilitated by use of a gas spring 44 arranged between the assembly 22 and an element or plate 70 rotating about the third axis 40. The spring 44 balances the weight of the X-ray tube assembly 14 on the one hand and the second film cassette tray 20 on the other hand. Thus, when the operator rotates the second film cassette tray 20 about the second horizontal axis 36, a corresponding rotation of the X-ray tube 10 will automatically result.

The three parallel horizontal axes 32, 36, and 40 are located below the lower end of the support column 26. The axes 32, 36 and 40 are fixed with respect to the mounting device 22.

The mounting device 22 basically contains an elongated horizontal carrier piece 48, an extension piece 50 extending downwardly from the left end thereof, a holding piece 52 and a connecting piece 54 connected to the carrier piece 48. The pieces 48, 50, 52 and 54 in actuality are a one-piece cast part. This part contains the axes 36 and 40. The three horizontal axes 32, 36 and 40 are arranged perpendicularly to the carrier piece 48. The first horizontal axis 32 is located at the lower end of the vertical extension piece 50. The second horizontal axis 36 is located at the right end of the carrier piece 48, and the third horizontal axis 40 is located between the second horizontal axis 36 and the first horizontal axis 32. In particular, the third horizontal axis 40 is provided in the upper portion of the vertical extension piece 50 as it joins with the horizontal support arm 48. These design features make sure that in the horizontal exposure position (see FIG. 2) the X-ray tube 10 and the second film cassette tray 20 are located below the lower end of the support column 26.

The sprocket and chain assembly 24 is a positioning device and simultaneously a transferring or moving device. The moving device for the X-ray tube 10 contains a first sprocket 56, a chain 57, and a second sprocket 58. The first sprocket 56 is firmly attached to the outer side of the support arm 30, and it is centered with respect to and rotatable about the first horizontal axis 32. The second sprocket 58 is rotatable about the third axis 40. Rotation is with respect to the carrier piece 48. The chain 57 connects the sprockets 56 and provides for a direct motion transfer.

The moving device for the film cassette tray 20 contains a third sprocket 59, a chain 60, and a fourth sprocket 61. The third sprocket 59 is firmly attached to the inner side of the support arm 34. It is centered with respect to and rotatable about the second horizontal axis 36. The fourth sprocket 61 is firmly attached to the outer side of the second sprocket 58 and rotatable therewith about the third axis 40. The chain 60 connects the sprockets 59 and 61 with each other and provides for a direct motion transfer. It is to be noted that the chain 60 connects the sprockets 59 and 61 crosswise. This chain fastening arrangement reverses the relative motion between the axes 36 and 40. This, in conjunction with the unreversed motion transfer between the axes 40 and 32, permits the simultaneous downward or upward motion of the film cassette tray 20 and the tube assembly 14.

Turnbuckles 62 and 63 are arranged within the chains 57 and 60, respectively. They independently permit adjustment of the tube assembly 14 and the cassette tray 20, respectively, for vertical and horizontal positioning requirements.

By means of the sprocket 56, 58, 59, 61 and chains 57, 60 a quick transition from a vertical exposure position (see FIG. 1) to a horizontal exposure position (see FIG. 2), and vice versa, can easily be performed. The spring 44 facilitates such a transition. This transition, therefore, does not require much strength on the part of the operator (physician, technician).

Due to the mechanical parts used which can be manufactured with only little play, a predetermined distance a between the focus 16 of the X-ray tube 10 and a film enclosed in the second film cassette tray 20 is achieved in the horizontal exposure position, even after a large number of transitions between the first and the second position. The distance a between the focus 16 and the second tray 20 may be, for instance, one meter. Due to the simplicity of the design, the X-ray apparatus can be operated very easily by the personnel (physician, X-ray assistant). This is especially true as far as adjustments with respect to the patient 2 are concerned. The X-ray apparatus including the transition mechanisms has a compact design which is of advantage for the personnel working on the patient 2.

A turntable or rotation device 74 is attached to the lower end of the telescopic support column 26. The device 74 is provided for rotating all elements attached thereto about the longitudinal axis 27 of the column 26. Thus, the whole X-ray assembly can be rotated about the vertical axis 27 in order to obtain a good adjustment with respect to the patient's body.

Firmly attached to the lower side of the rotating device 74 is a mounting arm 78. The mounting arm 78 extends in a horizontal direction. To its right end is attached a rotating device 80. The rotating device 80 supports an operating control box 82 which houses conventional control elements necessary for the operation of the X-ray apparatus. Thus, the control box 82 may be rotated about a horizontal axis. The box 82 may be provided with handles 98a and 98b (shown in FIG. 3) for performing such rotational movements. The left end of the mounting arm 78 is firmly connected to the piece 54 of the mounting device 22.

The lateral attachment device according to FIGS. 1 and 2 attaching the X-ray tube assembly 14 and the second film cassette tray 20 to the column 26 illustrates that conventional ceiling transports (see brochure "Ceiling Support," supra) which are already in use may be equipped with a lateral attachment, thereby making possible vertical and horizontal exposures.

Thus, one important feature of the embodiment illustrated in FIGS. 1 and 2 resides in the fact that the connection arm 54 and the elements directly or operationally connected therewith can easily be attached to the mounting arm 78. In the prior art design, the X-ray tube assembly 14 is directly connected to the mounting arm 78. Due to the present construction, such prior art design can easily be modified by removing the X-ray tube assembly 14 from the mounting arm 78, attaching it to the first support arm 30, and by attaching a completed unit comprising the arm 54 and front mounting bracket 84 to the end face of the mounting arm 78.

Figure 3:
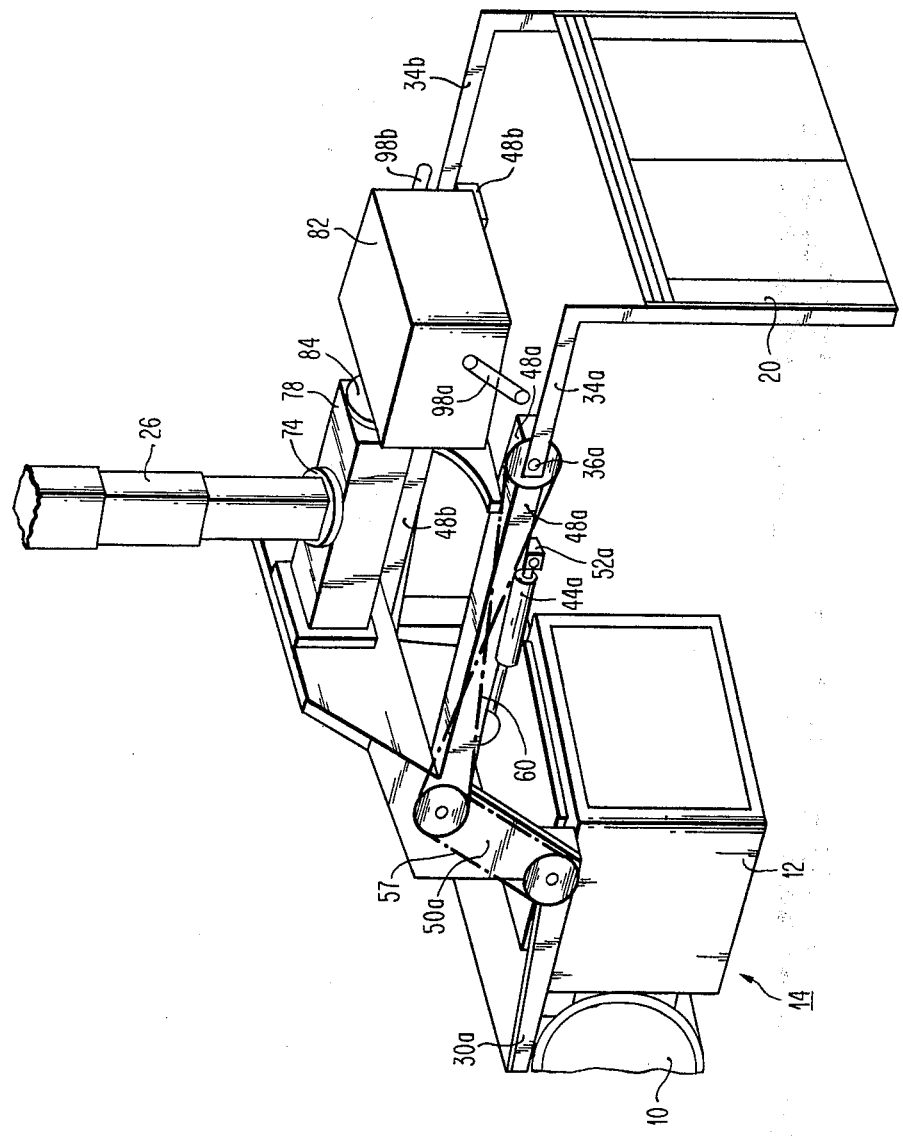
FIG. 3 is a perspective representation of the X-ray examination apparatus illustrated in FIG. 2.

In FIG. 3 is illustrated a perspective view of the X-ray apparatus shown in FIGS. 1 and 2. Those elements which are located on the front side (corresponding to FIGS. 1 and 2) of the X-ray apparatus are designated with a suffix "a", and those parts which are located at the rear side are denoted with a suffix "b".

From FIG. 3 it will be obvious that two parallel mechanisms are used for achieving coordinated transitions of the X-ray tube assembly 14 and the second X-ray film tray 20. The X-ray tube assembly 14 is supported by the parallel arms 30a 30b, while the second film cassette tray 20 is supported by the parallel arms 34a and 34b. The arm 30a is operatively connected to the arm 34a through a sprocket and chain mechanism, as illustrated in FIGS. 1 and 2. Similarly, the arm 30b is operatively connected to the arm 34b through a similar sprocket and chain mechanism designed in a mirror-inverted fashion with respect to the sprocket and chain mechanism illustrated in FIGS. 1 and 2.

In the X-ray examination apparatus of FIGS. 1 and 2 safety precautions are taken in order to prevent non-intended movements of the X-ray tube assembly 14 and the second cassette tray 20. These safety precautions include a locking device 81.

In FIG. 4 the locking device 81 for locking the X-ray tube 12 and the second tray 20 in their predetermined rotational positions is illustrated in detail. In accordance with FIG. 1, an element or plate 70 is provided with apertures 90 and 92 on the plate rim. These apertures 90 and 92 are spaced approximately 90° apart from each other. The plate 70 is rotatable about the third horizontal axis 40 which is represented by a shaft 93. The plate 70 and the sprockets 58 and 61 are firmly connected to the shaft 93. Thus, the plate 70 is rotated whenever the sprockets 58 and 61 are rotated.

An actuation rod 96 is provided to slide in sleeve bearings 98 and 100 of blocks or cross support members 102 and 104, respectively, and to extend into any of the two apertures 90 and 92. Both cross support members 102 and 104 are fastened on or connected to the support arm 48. The actuation rod 92 can be retracted by a lever 108. The lever 108 is rotatable about a lever pivot 110 which is fixed with respect to the support arm 48. The lever 108 can be pulled down by the operator. This removes the actuation rod 96 from the aperture 90 or 92. That is, by pulling the lever 108 in the direction of the arrow 112, the actuation rod 96 is retracted from the aperture 90 or 92, thereby releasing the plate 70 for rotation.

In order to insert the actuation rod 96 firmly into any of the apertures 90 and 92, a spring 114 is provided on the actuation rod 96. The spring 114 is biased against the cross support member 102 and against a washer 116 fixed on the rod 96.

In the vertical X-ray emission position, the aperture 90 is aligned with the actuation rod 96. In this position, the rod 96 extends into the aperture 90, thereby preventing the plate 70 from rotating about the third horizontal axis 40. In the horizontal X-ray position, however, which is assumed in FIG. 4, the aperture 92 is aligned with the actuation rod 96. The rod 96 now extends into this aperture 92, thereby again preventing the plate 70 from rotating about the third horizontal axis 40. Thus, the locking device 81 locks the X-ray tube 10 in its first and second position.

While the form of the X-ray apparatus herein described constitutes preferred embodiments of the invention, it is to be understood that the invention is not limited to these precise form of assembly, and that a variety of changes may be made therein without departing from the scope of the invention.

What is claimed is:

1. In an X-ray apparatus containing:
an X-ray tube;
a support for said tube; means for moving said X-ray tube between
a first position in which said X-ray tube is adapted to emit a beam of X-rays in a first direction, and
a second position in which said X-ray tube is adapted to emit a beam of X-rays in a second direction substantially normal to said first direction;
a film cassette tray having a plane in an exposure position to receive said beam of X-rays from said X-ray tube when said X-ray tube is in its second position; and
sprocket and chain means operationally connected to said X-ray tube support for positioning said film cassette tray in a waiting position outside said beam of X-rays when said X-ray tube is in its first position and for transferring said film cassette tray from said waiting position to said exposure position when said X-ray tube is moved from its first position to its second position.

2. The improvement according to claim 1, further comprising:
a support column positioned above said X-ray apparatus;
a mounting device connected to said column, said mounting device having a first and a second side, said sides being opposite to each other with respect to the longitudinal axis of said support column, wherein said X-ray tube is arranged on said first side and said film cassette tray is arranged on said second side;
first pivoting means for pivotally attaching said X-ray tube to said mounting device, said X-ray tube thereby being tiltable about a first horizontal axis between said first and said second position; and
second pivoting means for pivotally attaching said film cassette tray to said mounting device, said tray thereby being tiltable about a second horizontal axis between said waiting position and said exposure position, said first and second axes being parallel to each other.

3. The improvement according to claim 2, wherein said sprocket and chain means comprises:
a first sprocket rotatable about said first horizontal axis;
a second sprocket rotatable about a common horizontal axis;
a third sprocket rotatable about said second horizontal axis;
a fourth sprocket also rotatable about said said common horizontal axis;
a first chain connecting said first and second sprockets; and
a second chain connecting said third and fourth sprockets, whereby one of said first and second chains connects the respective sprockets crosswise.

4. The improvement according to claim 2, wherein said mounting device comprises locking means for locking said X-ray tube in said first position and in said second position.

5. The improvement according to claim 4, wherein said locking means comprises an actuation rod and a plate rotatable about said common rotation axis, said plate having two apertures for receiving one end of said rod in a respective one of said first and second positions.

6. The improvement according to claim 2, wherein in said waiting position said film cassette tray extends approximately horizontally, wherein in said first position said X-ray tube is adapted to emit said X-ray beam substantially vertically, and wherein in said second position said X-ray tube is adapted to emit said X-ray beam substantially horizontally.

7. The improvement according to claim 2, wherein said X-ray tube is attached to at least one first arm, one end portion of which is tiltable about said first horizontal axis, and wherein said cassette tray is attached to at least one second arm, one end portion of which is tiltable about said second horizontal axis.

8. The improvement according to claim 2, wherein said sprocket and chain means comprises two systems which are arranged parallel to each other.

* * * * *